United States Patent [19]

Dragan

[11] Patent Number: 5,273,426
[45] Date of Patent: Dec. 28, 1993

[54] TRANSFORMABLE ORTHODONTIC O-RING DISPENSER

[76] Inventor: William B. Dragan, 85 Burr St., Easton, Conn. 06612

[21] Appl. No.: 903,760

[22] Filed: Jun. 25, 1992

[51] Int. Cl.⁵ .................................................. A61C 7/00
[52] U.S. Cl. .......................................... 433/18; 433/11
[58] Field of Search ............... 433/4, 11, 18; 206/820; 2/319, 338

[56] References Cited

U.S. PATENT DOCUMENTS

| | | | |
|---|---|---|---|
| 2,680,497 | 6/1954 | Miller | 206/820 |
| 2,986,396 | 5/1961 | Abbott et al. | 2/319 |
| 3,016,136 | 1/1962 | Poupitch | 206/820 |
| 3,241,658 | 3/1966 | Anderson | 206/820 |
| 4,038,753 | 8/1977 | Klein | 433/18 |
| 4,412,820 | 11/1983 | Brummond et al. | 433/18 |
| 4,939,932 | 6/1990 | Cleary | 433/18 |
| 4,946,385 | 8/1990 | Eckert et al. | 433/18 |
| 4,946,386 | 8/1990 | Kidd et al. | 433/18 |
| 5,108,008 | 4/1992 | Ryder | 206/820 |

Primary Examiner—Paul J. Hirsch
Attorney, Agent, or Firm—Paul A. Fattibene; Arthur T. Fattibene

[57] ABSTRACT

An orthodontic O-ring holder that can be transformed from a linear shape to a ring shape having a central tree or core with a plurality of orthodontic O-rings attached thereto. The orthodontic O-rings are frangibly attached to the central tree or core for ease of separation, and coupling means are provided for latching the opposed ends of the linear tree together to form a ring shaped dispenser. Therefore, the doctor can use the orthodontic O-ring dispenser in either a linear or ring form, depending upon the doctor's preference or application. The entire assembly is made of an elastic material.

7 Claims, 2 Drawing Sheets

TRANSFORMABLE ORTHODONTIC O-RING DISPENSER

FIELD OF THE INVENTION

The present invention relates generally to hand-held orthodontic O-ring dispensers, and more particularly to an orthodontic O-ring dispenser that can be configured into a ring.

DESCRIPTION OF THE PRIOR ART

Orthodontic O-rings are used in many orthodontic procedures. Due to the small size of orthodontic O-ring's, between 3 and 4 millimeters, handling of these O-rings is difficult. Therefore, there have been devised many types of dispensers for assisting the doctor in handling these small O-rings. One such device is disclosed in U.S. Pat. No. 4,217,686 issuing to Dragan on Aug. 19, 1980 and entitled "Orthodontic O-Ring and Ligator Therefor", which is herein incorporated by reference. Therein disclosed is a linear O-ring tree having orthodontic O-rings frangibly attached thereto. The doctor dispenses the O-rings attached to the tree by wrapping a portion of the linear tree around his hand or finger. Often, the doctor has difficulty holding such linear tree of orthodontic O-rings while performing work on a patient. Other types of dispensers for orthodontic O-rings have been developed. Such other orthodontic O-ring dispensers have been substantially disk-shaped. One such example of a disk-shaped orthodontic O-ring dispenser is disclosed in U.S. Pat. No. 4,934,932 issuing to Cleary on Jun. 19, 1990 and entitled "Dispenser for Orthodontic O-Rings." Therein disclosed is a disk shape orthodontic O-ring dispenser that can be held between the thumb and forefinger, which is incrementally rotated for dispensing of the attached O-rings.

While such orthodontic O-ring dispensers have accomplished the purpose for which they have been intended, no one dispenser has satisfied all of the needs of the doctor. Therefore, there is a need for an orthodontic O-ring dispenser that can be easily held and adjusted to the doctor's individual preferences.

SUMMARY OF THE INVENTION

The present invention is an orthodontic O-ring dispenser that can transform from a linear dispenser into a ring shaped dispenser to facilitate the holding and dispensing of the O-rings. The ring shaped dispenser can easily be positioned over the doctor's finger so that it can easily be held while working on a patient. The present invention comprises a linear tree having O-rings attached thereto. The O-rings are attached to the tree or holder by a frangible or weakened portion. Thereby, the O-rings can easily be removed from the tree or holder when needed. Coupling means are attached to either end of the linear tree or holder for attaching the ends together, thereby forming a ring. In the preferred embodiment, the coupling means is comprised of a locking member formed on one end of the linear tree that can be pushed through a catching member in the form of an annular member formed on the other end of the linear tree. Therefore, the O-ring dispenser of the present invention is transformable from a linear O-ring dispenser into a ring shaped O-ring dispenser, thereby providing the doctor with flexibility in how to hold the O-ring dispenser while working on a patient. The doctor can either wrap the linear dispenser around his hand or finger, or form a ring to be placed around a finger.

Accordingly, it is an object of the present invention to provide an orthodontic O-ring dispenser that is easy to hold.

It is an advantage of the present invention that the O-ring dispenser can be transformed or adapted to the individual preferences of the doctor.

It is another advantage of the present invention that the molds for the manufacture of the O-ring dispenser are more inexpensive to produce than circular or disc shaped molds.

It is yet another advantage of the present invention that if all of the O-rings are not used in a single visit of a patient, then the O-ring dispenser can be uncoupled and placed in the patients file, thereby preventing waste and the possibility of cross contamination.

It is a feature of the present invention that coupling means are provided for attaching the opposed ends of a linear O-ring dispenser together for forming a ring shaped dispenser.

It is another feature of the present invention that the O-rings are dispensed in a plane perpendicular to the plane of the O-ring dispenser when configured in a ring shape.

These and other objects, advantages, and feature will become readily apparent in view of the following more detailed description.

DETAILED DESCRIPTION OF THE PREFERRED EMBODIMENTS

Figure 1:
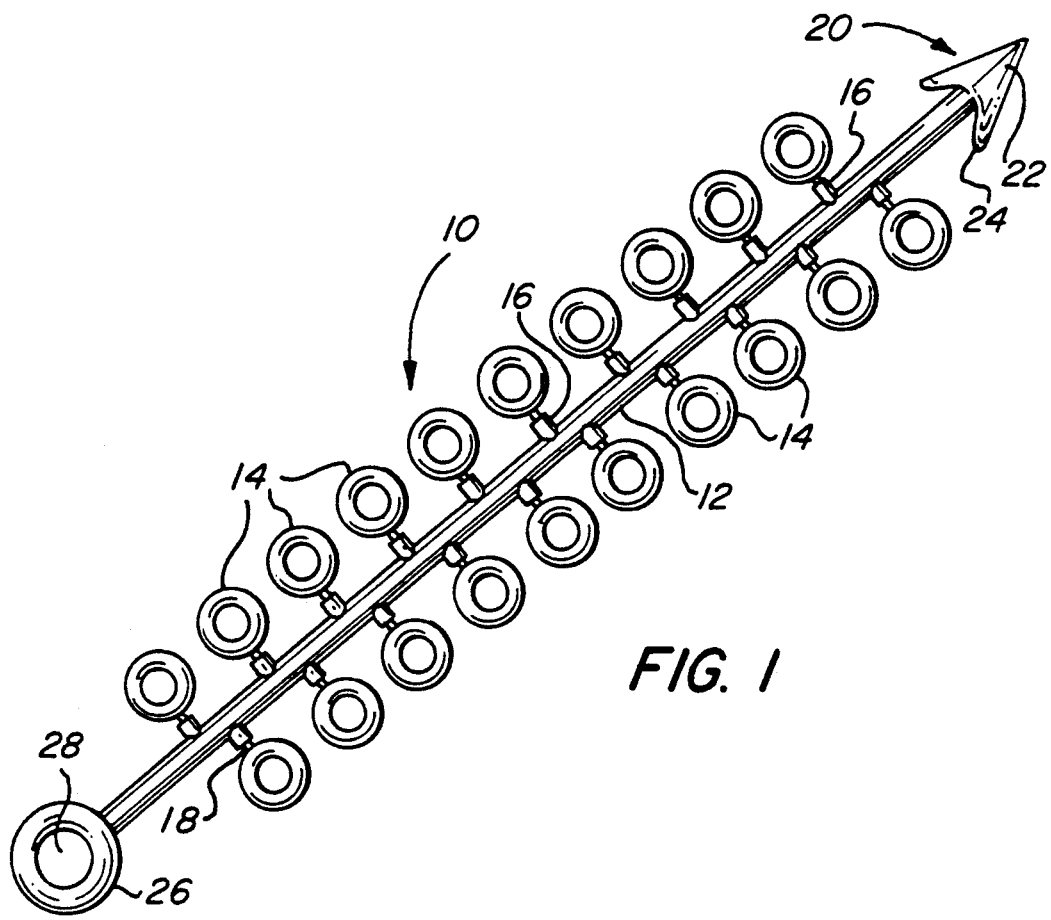
FIG. 1 is a plan view of the present invention in linear form.

FIG. 1 illustrates the O-ring assembly 10 of the present invention. The O-ring assembly 10 is comprised of a tree or core 12. Attached to the tree 12 are O-rings 14. The O-rings 14 are attached to the tree 12 by a readily frangible connection. As illustrated, branches 16 are projected from the tree or core to which the O-rings 14 are attached by frangible or weakened portion 18. It will be understood that the frangible connection may be directly connected between the core or tree 12 and the O-ring 14.

On one end of the linear O-ring assembly 10 is a latching member shaped as an arrow 20. The arrow 20 has a point 22 and barbs 24. At the other end of linear O-ring assembly 10 is a latching ring or circular shaped member 26 having a center 28. Hole 28 has a diameter sufficiently large to permit arrow or latching end 20 to pass therethrough. However, hole 28 has a diameter sufficiently small so that once arrow 20 is passed therethrough, the barbs 24 on arrow 20 prevent arrow 20 from easily re-passing therethrough.

The entire O-ring assembly 10 is made of elastic material. This permits convenient and economical manufacturing. The elastic O-rings 14 are easily removed by hand and/or with a tool, such as a ligator. The number of O-rings which are integrally molded to a single tree 12 may be varied, depending upon the application.

Figure 2:
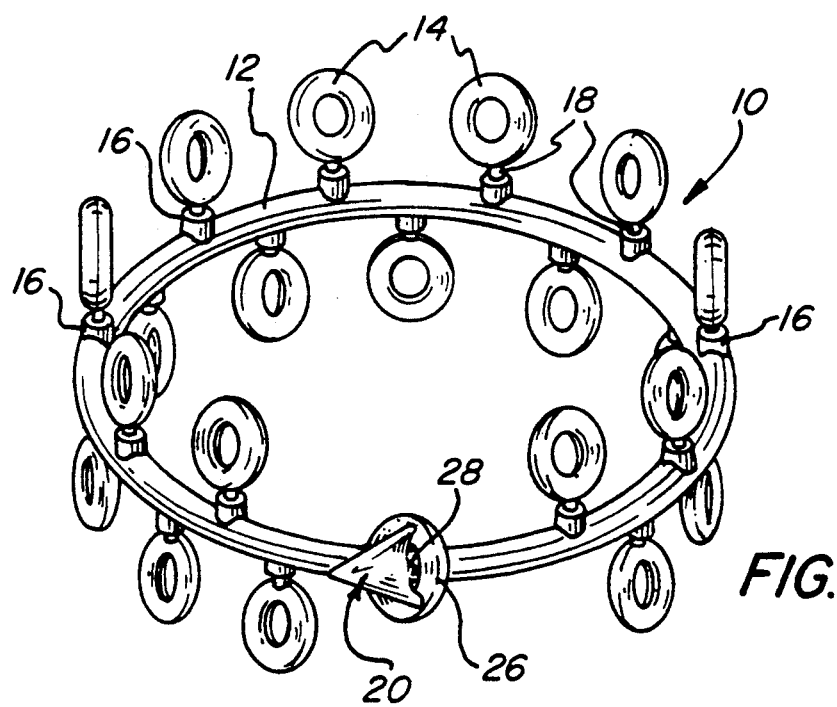
FIG. 2 is a perspective view of the present invention transformed into a ring.

FIG. 2 illustrates the present invention assembled in its ring formation. In this arrangement, the ring formation can be placed on the doctor's finger to facilitate holding the same as the attached O-rings 14 are readily dispensed while working on a patient.

It should be noted that the plane in which the ring formed by core or tree 12 is positioned is perpendicular to the plane in which the O-rings are positioned. This facilitates dispensing of the O-rings by the doctor when the present invention is in a ring shape and placed around the doctor's finger.

The arrow 20 and latching ring 26 provide detachable coupling means for connecting the opposed ends of the tree or core together to form a ring. The coupling means can take other well known shapes. However, the arrow 20 and donut or ring 26 are illustrated as the preferred embodiment because of its simplicity of use and ease of manufacture.

Figure 3:
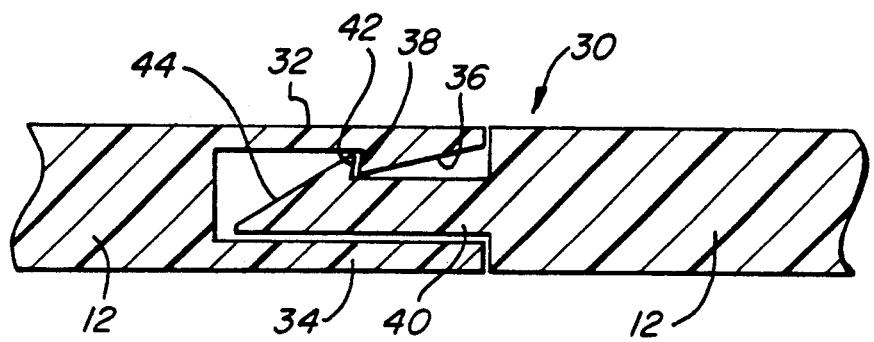
FIG. 3 is a cross-section of a portion of the present invention illustrating another embodiment for coupling the ends of the O-ring dispenser together.

FIG. 3 illustrates another embodiment of a complimentary coupling means. Coupler 30 has a female end comprising an upper portion 32 and a lower portion 34. Upper portion 32 has an upper ramp 36 and an upper shoulder 38. Male end 40 has a lower shoulder 42 and a lower ramp 44. Coupler 30 has a rectangular cross-section. In operation, male end 40 is inserted into the female end comprising upper portion 32 and lower portion 34. Coupler 30 is made of the same material as the elastic O-rings and, is therefore somewhat flexible. Therefore, the upper shoulder 38 and lower shoulder 42 are caused to mate, locking the ends together so that a ring is formed by the core 12.

Figure 4:
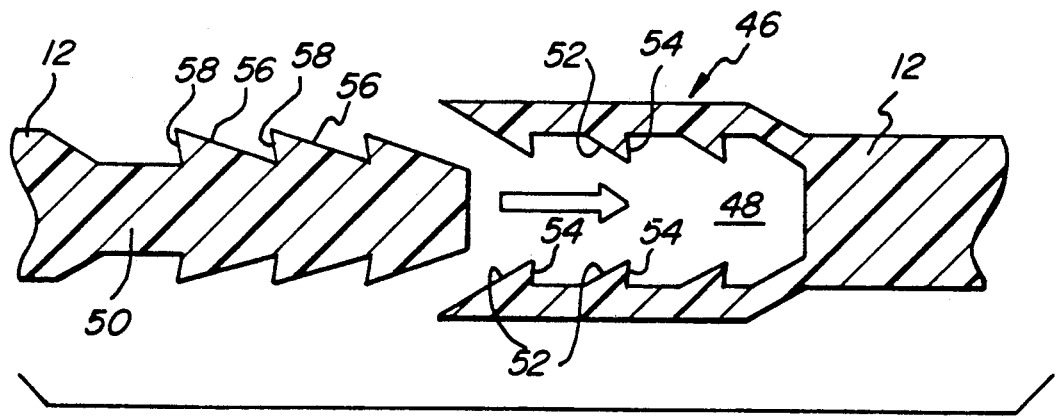
FIG. 4 is a cross-section of a portion of the present invention illustrating yet another embodiment for coupling the ends of the O-ring dispenser together.

FIG. 4 illustrates yet another embodiment of a complimentary coupling means. The coupler 46 has a female portion 48 and a male portion 50. Within female portion 48 are a series of ramps 52 and shoulders 54. The male portion 50 has similar complimentary ramps 56 and complimentary shoulders 58. The cross-section of coupler 46 is circular. When male portion 50 is inserted into female portion 46, the shoulders 52 and complimentary shoulders 58 interlock, causing the female portion 48 and male portion 50 to lock together so that a ring is formed from core 12.

It should readily be appreciated that the present invention provides the doctor with a convenient O-ring dispenser that can be readily utilized and transformed to meet the doctor's individual needs or preferences. The doctor can either use the O-ring assembly 10 in linear form or easily and conveniently form a ring to be held on a finger whereby the present invention is rendered readily adaptable to the particular needs or preferences of the doctor.

While the present invention has been described with respect to particular embodiments, it will be readily understood and appreciated that variations and modifications may be made without departing from the spirit and scope of this invention.

What is claimed is:

1. A transformable orthodontic O-ring assembly for dispensing orthodontic O-rings comprising:
   an elongated flexible tree having a first and second end;
   a plurality of miniature elastic orthodontic O-rings;
   a readily frangible connection for attaching each of said O-rings to said tree at spaced apart intervals there along, said frangible connection having a weakened portion adjacent the circumference of the attached O-ring; and
   complementary coupling means, associated with the first and second ends, for attaching the first and second ends together forming a ring.

2. A transformable orthodontic O-ring assembly as in claim 1 wherein:
   the orthodontic O-ring assembly is made of a unitary casting of the same material.

3. A transformable orthodontic O-ring assembly as in claim 1 wherein:
   the orthodontic O-ring assembly is made of an elastic material.

4. A transformable orthodontic O-ring assembly as in claim 1 wherein said coupling means comprises:
   a latching arrow attached to the first end; and
   a ring attached to the second end for receiving said latching arrow.

5. A transformable orthodontic O-ring assembly as in claim 1 wherein:
   each of said plurality of orthodontic O-rings have an outside diameter of at least three millimeters.

6. A transformable orthodontic O-ring assembly for dispensing orthodontic O-rings comprising:
   an elongated flexible tree having a first and second end;
   a plurality of miniature elastic orthodontic O-rings;
   a readily frangible connection for attaching each of said O-rings to said tree at spaced apart intervals there along, said frangible connection having weakened portion adjacent the circumference of the attached O-ring; and
   complementary coupling means, associated with the first and second ends, for attaching the first and second ends together forming a ring, said complementary coupling means attaching together such that the plane formed by the ring is perpendicular to the plane of each of said plurality of miniature elastic orthodontic O-rings.

7. A transformable orthodontic O-ring assembly for dispensing orthodontic O-rings as in claim 6 wherein:
   said plurality of miniature elastic orthodontic O-rings are formed in at least two rows along said elongated flexible tree.

* * * * *